(12) United States Patent
Miyamura et al.

(10) Patent No.: US 10,143,765 B2
(45) Date of Patent: Dec. 4, 2018

(54) DEODORIZER, DEODORIZING PROCESSED PRODUCT PRODUCED USING SAME, METHOD FOR PRODUCING DEODORIZER, AND METHOD FOR PRODUCING DEODORIZING PROCESSED PRODUCT

(71) Applicant: TOAGOSEI CO., LTD., Tokyo (JP)

(72) Inventors: Kentarou Miyamura, Nagoya (JP); Koji Sugiura, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 0 days.

(21) Appl. No.: 15/522,424

(22) PCT Filed: Oct. 5, 2015

(86) PCT No.: PCT/JP2015/078198
§ 371 (c)(1),
(2) Date: Apr. 27, 2017

(87) PCT Pub. No.: WO2016/067839
PCT Pub. Date: May 6, 2016

(65) Prior Publication Data
US 2017/0312381 A1    Nov. 2, 2017

(30) Foreign Application Priority Data
Oct. 31, 2014    (JP) .................................. 2014-223220

(51) Int. Cl.
| A61L 9/014 | (2006.01) |
| A61L 9/01 | (2006.01) |
| A61L 9/16 | (2006.01) |
| B01J 20/16 | (2006.01) |
| B01J 20/18 | (2006.01) |
| B01J 20/30 | (2006.01) |
| C08K 3/34 | (2006.01) |

(52) U.S. Cl.
CPC ................. *A61L 9/014* (2013.01); *A61L 9/01* (2013.01); *A61L 9/16* (2013.01); *B01J 20/16* (2013.01); *B01J 20/18* (2013.01); *B01J 20/183* (2013.01); *B01J 20/30* (2013.01); *B01J 20/3078* (2013.01); *C08K 3/34* (2013.01)

(58) Field of Classification Search
None
See application file for complete search history.

(56) References Cited

U.S. PATENT DOCUMENTS

| 6,414,071 B1 * | 7/2002 | Wypart ..................... C08K 3/34 524/450 |
| 2001/0012820 A1 | 8/2001 | Nishijima et al. |
| 2010/0071597 A1 * | 3/2010 | Perez-Pena ........... C04B 28/021 106/708 |
| 2010/0203284 A1 * | 8/2010 | Kanai ..................... C04B 28/24 428/116 |
| 2012/0167804 A1 * | 7/2012 | Perez-Pena ........... C04B 18/027 106/677 |
| 2012/0172469 A1 * | 7/2012 | Perez-Pena ........... C04B 28/021 521/83 |
| 2012/0190534 A1 * | 7/2012 | Itabashi .................. C01B 39/46 502/60 |

FOREIGN PATENT DOCUMENTS

| JP | H01171554 A * | 7/1988 | ............... A61L 9/01 |
| JP | 1-171554 A | 7/1989 | |
| JP | 10-226962 A | 8/1998 | |
| JP | 2001-170150 A | 6/2001 | |
| JP | 2001-286752 A | 10/2001 | |
| JP | 2003-126229 A | 5/2003 | |
| JP | 2004-24330 A | 1/2004 | |
| JP | 2006-273694 A | 10/2006 | |
| JP | 2007-215818 A | 8/2007 | |
| JP | 2007-320576 A | 12/2007 | |
| JP | 2008-178788 A | 8/2008 | |
| WO | WO 2004/058311 A1 | 7/2004 | |
| WO | WO 2013/182974 A1 | 12/2013 | |

OTHER PUBLICATIONS

International Search Report for PCT/JP2015/078198 dated Dec. 28, 2015.
Written Opinion of the International Searching Authority for PCT/JP2015/078198 (PCT/ISA/237) dated Dec. 28, 2015.
Bao et al., "Adsorption equilibria of $CO_2$, $CH_4$, $N_2$, $O_2$, and Ar on high silica zeolites," Journal of Chemical & Engineering Data, vol. 56, No. 11, Oct. 7, 2011, pp. 4017-4023.
Extended European Search Report for corresponding Application No. 15855261.2, dated Jun. 25, 2018.

* cited by examiner

*Primary Examiner* — Peter A Salamon
(74) *Attorney, Agent, or Firm* — Birch, Stewart, Kolasch & Birch, LLP

(57) ABSTRACT

Provided are: a deodorizer that has high VOC-adsorbing performance and can exhibit deodorizing properties even in a case in which the deodorizer is kneaded into resin, a deodorizing processed product produced by using the deodorizer, and a method for producing the deodorizer. The deodorizer of the present invention is characterized by including a zeolite represented by the following Formula [1], in which the zeolite is obtained by producing a zeolite and then heating the produced zeolite at a temperature of from 120° C. to 250° C.: $xNa_2O \cdot Al_2O_3 \cdot ySiO_2 \cdot zH_2O$ [1]. In Formula [1], x represents a positive number of from 0.5 to 5.0, y represents a positive number of from 80 to 150, and z represents a positive number of from 1 to 20.

5 Claims, No Drawings

DEODORIZER, DEODORIZING PROCESSED PRODUCT PRODUCED USING SAME, METHOD FOR PRODUCING DEODORIZER, AND METHOD FOR PRODUCING DEODORIZING PROCESSED PRODUCT

TECHNICAL FIELD

The present invention relates to a deodorizer that has high performance for adsorbing volatile organic compounds (hereinafter referred to as "VOC") and that includes a heat-resistant inorganic compound, a deodorizing processed product using the deodorizer, and methods for producing the deodorizer and deodorizing processed product.

BACKGROUND ART

In recent years, there have been seen concerns about health hazards due to VOCs, as seen in sick house/sick building syndromes and the like. To prevent this, it is known that an aldehyde adsorbents composed of an amine compound or an ammonium salt is effective in removing an aldehyde-based gas in room environments. Additionally, Patent Document 1 to 5 and the like disclose that techniques for improving adsorbability by supporting such an amine compound or an ammonium salt on an inorganic compound.

On the other hand, it is known that a zeolite that includes only an inorganic compound without any amine compound, any ammonium salt, or the like is effective as a deodorizer. For example, Patent Document 6 discloses deodorizing effect of a zeolitic aluminosilicate represented by chemical composition $xM_{2/m}O \cdot Al_2O_3 \cdot ySiO_2 \cdot nH_2O$ on hydrogen sulfide, ammonia, methyl sulfide, and ethyl mercaptan. Patent Document 7 discloses a deodorizing method in which a porous material having a peak pore diameter distribution within a pore diameter range of from 4.0 to 7.1 angstroms (Å) (1 Å is equal to 0.1 nm) is allowed to adsorb acetaldehyde, and describes zeolites having a $SiO_2/Al_2O_3$ molar ratio of 100 or more as porous materials.

Furthermore, Patent Document 8 discloses a high-silica zeolite including, as an exchangeable cation, at least one selected from the group consisting of alkali metals and alkali earth metals and having a silica/alumina ratio of 20 or more, which is an adsorbing/capturing zeolite in which after boiling a 5 mass % zeolite aqueous suspension prepared by using deionized water for 5 minutes, the obtained aqueous suspension has an electric conductivity of 400 µs/cm or less, and an oxygen adsorbing container containing the zeolite.

CITATION LIST

Patent Document

Patent Document 1: JP-A No. 2007-215818 (JP-A denotes a Japanese unexamined patent application publication)
Patent Document 2: JP-A No. H10-226962
Patent Document 3: WO 2004/058311
Patent Document 4: JP-A No. 2008-178788
Patent Document 5: JP-A No. 2001-286752
Patent Document 6: JP-A No. H01-171554
Patent Document 7: JP-A No. 2003-126229
Patent Document 8: JP-A No. 2006-273694

DISCLOSURE OF THE PRESENT INVENTION

Problems that the Present Invention is to Solve

However, powdery adsorbents as disclosed in Patent Document 1 to 5 are adsorbents specialized in deodorizing an aldehyde gas, and there is a problem in that when the absorbents are heated to approximately 200° C., adsorbing performance is reduced, and furthermore, discoloring occurs. Additionally, the above absorbents are inferior in heat resistance, and therefore sufficient deodorizing performance cannot be obtained in uses involving kneading into resin and exposure to high temperature.

In the deodorizer described in Patent Document 6, VOC-adsorbing performance and heat resistance are unknown. Heat resistance of the zeolite of Patent Document 7 is unknown, and there is no description regarding deodorizing properties when kneaded into resin. Furthermore, while Patent Document 8 has disclosed a resin-molded article containing zeolite, VOC deodorizing properties have not been described therein.

The zeolite described in Patent Document above is the porous material having the pore diameter of several angstroms (Å). It is thus apparent that the zeolite has an ability to adsorb VOC similar in size, but there are few cases of use by kneading into resin. The speculated reason for this is that deodorizing performance of zeolite is reduced even when simply processed into resin, and therefore zeolite lacks practicality.

The present invention has been accomplished in view of the above problems. An object of the invention is to provide a deodorizer that has high VOC-adsorbing performance and that exhibits deodorizing properties even in a case in which the deodorizer is kneaded into resin, a deodorizing processed product using the deodorizer, a method for producing the deodorizer, and a method for producing the deodorizing processed product.

The inventors of the present invention found that by heating a zeolite having a specific composition among conventionally known zeolites, VOC-adsorbing performance is improved and heat resistance becomes excellent, thereby completing the invention.

Specifically, the invention is as follows:

<1> A deodorizer comprising a zeolite represented by the following Formula [1],
wherein the zeolite is obtained by producing a zeolite and then heating the produced zeolite at a temperature of 120° C. to 250° C.:

$$x\text{Na}_2\text{O} \cdot \text{Al}_2\text{O}_3 \cdot y\text{SiO}_2 \cdot z\text{H}_2\text{O} \qquad [1]$$

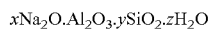

wherein x represents a positive number of from 0.5 to 5.0, y represents a positive number of from 80 to 150, and z represents a positive number of from 1 to 20.

<2> A deodorizer composition comprising the deodorizer according to <1> and at least one of a basic gas deodorizer or a sulfur gas deodorizer.

<3> A deodorizing processed product including the deodorizer according to <1>.

<4> A method for producing a deodorizer comprising, in the following order:
a production step of producing a zeolite; and
a heating step of heating the zeolite obtained at the production step at a temperature of 120° C. to 250° C. to obtain a zeolite represented by Formula [1]:

$$x\text{Na}_2\text{O} \cdot \text{Al}_2\text{O}_3 \cdot y\text{SiO}_2 \cdot z\text{H}_2\text{O} \qquad [1]$$

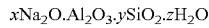

wherein x represents a positive number of from 0.5 to 5.0, y represents a positive number of from 80 to 150, and z represents a positive number of from 1 to 20.

<5> A method for producing a deodorizing processed product comprising: producing a zeolite represented by Formula [1], then heating the zeolite at a temperature of 120° C. to 250° C. before processing, and blending the obtained zeolite in a resin, a fiber, a paint, or a sheet.

Advantageous Effects of Invention

The deodorizer of the invention has high VOC-adsorbing performance and is also excellent in heat resistance, so that the deodorizer can exhibit deodorizing effect after being kneaded into resin.

MODE FOR CARRYING OUT THE PRESENT INVENTION

Embodiments of the present invention will be described hereinafter, but the invention is not limited thereto. In addition, "%" indicates "% by mass", and "parts" indicates "parts by mass" unless otherwise noted. In the present specification, in a case in which a numerical range is indicated by using "to", the numerical range means a range including a lower limit value and an upper limit value described before and after "to".

1. Deodorizer

A deodorizer of the invention is characterized by including a zeolite represented by the following Formula [1], in which the zeolite is obtained by producing a zeolite and then heating the produced zeolite at a temperature of 120° C. or more:

$$xNa_2O.Al_2O_3.ySiO_2.zH_2O \quad [1]$$

wherein x represents a positive number of from 0.5 to 5.0, y represents a positive number of from 80 to 150, and z represents a positive number of from 1 to 20.

Hereinafter, constituent components of the invention will be specifically described.

(1) Zeolite

The zeolite included in the deodorizer of the invention is a compound represented by Formula [1] above. In Formula [1], the ratio of $Na_2O$ represented by x is from 0.5 to 5.0, and preferably from 0.7 to 3.0. As an alternative to Na, an other alkali metal, alkali earth metal, ammonia, or hydrogen can be included. However, in order to exhibit VOC-adsorbing performance and heat resistance, $Na_2O$ is excellent, to the performance and resistance and thus it is necessary to include a certain amount of $Na_2O$. From the viewpoint of VOC-adsorbing performance, the ratio of $SiO_2$ represented by y ($SiO_2/Al_2O_3$ molar ratio) is from 80 to 150, preferably from 90 to 130, and more preferably from 95 to 120. In addition, from the viewpoint of VOC-adsorbing performance, foam suppression in resin molding, and the like, the ratio of $H_2O$ represented by z is from 1 to 20, and more preferably from 3 to 15.

It is possible to produce the deodorizer of the invention so that the zeolite has a median diameter in a range of from 0.5 to 5 μm. The median diameter is preferably from 1 to 3 μm, and more preferably from 1 to 2 μm. In addition, when considering processability into various products, such as spinning by kneading into fiber, not only the median diameter but also a maximum particle diameter is important. Thus, the maximum particle diameter of the zeolite represented by Formula [1] above is preferably 10 μm or less, and particularly preferably 8 μm or less from the viewpoint that processability and deodorizing effect are easily exhibited.

The zeolite included in the deodorizer of the invention has a BET specific surface area of preferably from 300 to 450 $m^2/g$, and more preferably from 320 to 420 $m^2/g$. When the BET specific surface area thereof is within the range of from 300 to 450 $m^2/g$, VOC-adsorbing performance is further improved, so that deodorizing effect is enhanced.

A target to be adsorbed by the deodorizer of the invention is VOC that is an organic substance having a boiling point of approximately from 0° C. to 260° C. Specific examples of the VOC include toluene, xylene, 1,3,5-trimethylbenzene, decane, methanol, dichloromethane, methyl ethyl ketone, n-butane, isobutane, trichloroethylene, isopropyl alcohol, butyl acetate, acetone, methyl isobutyl ketone, isophorone, cyclohexane, ethanol, methylcyclopentane, vinyl acetate, 3-methylhexane, 2,3-dimethylbutane, tetrafluoroethylene, ethylbenzene, cumene, butyl cellosolve, n-hexane, n-butanol, n-pentane, isobutanol, styrene, tetrachloroethylene, propane, butane, formaldehyde, acetaldehyde, acrolein, hexanol, nonenal, ethyl acetate, and diacetyl.

(2) Method for Producing Deodorizer

A method for producing a deodorizer of the invention comprises a production step of producing a zeolite (hereinafter referred to also simply as "production step") and a heating step of heating the zeolite obtained at the production step at a temperature of 120° C. or more to obtain a zeolite represented by Formula [1] (hereinafter referred to also simply as "heating step") in this order.

Hereinafter, each of the steps will be described.

[Production Step]

The method for producing a deodorizer of the invention includes the production step of producing a zeolite.

As the method for producing a zeolite in the production step, any known method can be used.

For example, a method for producing a zeolite known as an MFI type synthetic high silica zeolite is used. In other words, the zeolite produced in the present production step is preferably an MFI type synthetic high silica zeolite.

For example, the zeolite can be produced by enclosing an aqueous mixture containing tetra-lower alkoxysilane as a silica source, an alumina source, and tetrapropyl ammonium salt as an alkali metal source and a crystallizing agent in a pressure-resistant vessel and maintaining at a hydrothermal synthesis temperature of from 160 to 200° C.

Specifically, the aqueous mixture (sol or gel) as the component of a synthetic mother liquid consists of a silica source, an alumina source, an alkali metal source, a crystallizing agent, and water. Examples of tetra-lower alkoxysilane as the silica source include tetramethoxysilane, tetraethoxysilane, tetraisopropoxy silane, and tetra-n-butoxy silane. Preferred is tetraethoxysilane, which is hydrolyzed to form $SiO_2$. Examples of the alumina source include sodium aluminate, aluminum nitrate, aluminum sulfate, and alumina powder. Typically, sodium aluminate is used, and, in this case, can also serve as an alkali metal source. Typical examples of the alkali metal source include sodium hydroxide and potassium hydroxide. Examples of the crystallizing agent (a structure controlling agent) include tetrapropylammonium salts having a molecular size and a structure suitable to form a zeolite, and typically, tetrapropylammonium bromide is used. In the case of other tetra-lower alkylammonium salts, zeolite is not formed.

The synthetic mother liquid including these respective components and water is typically used as an aqueous mixture having the following composition ratio (molar ratio):

$SiO_2/Al_2O_3$=approximately from 40 to 250
Crystallizing agent/$SiO_2$=approximately from 0.05 to 1.0
$Na_2O/SiO_2$=approximately from 0.01 to 1.0
$H_2O/SiO_2$=approximately from 10 to 400

The synthetic mother liquid (aqueous mixture) including these respective components can be prepared, for example, by the following method:

(1) Tetra-lower alkoxysilane is added and stirred in an aqueous solution in the presence of an acid catalyst such as nitric acid or hydrochloric acid to perform hydrolysis reaction, thereby forming $SiO_2$.

(2) An aqueous solution including an alkali metal source is added to the hydrolysis reaction solution.

(3) Separately from the above, an aqueous solution including a crystallizing agent is added to an aqueous solution including an alumina source, and the mixture is stirred.

(4) The solution prepared in (3) is added to the solution prepared in (2) above, and the obtained mixture is stirred at room temperature for approximately from 6 to 24 hours.

The aqueous mixture as the component of the synthetic mother liquid is enclosed in a pressure-resistant container such as an autoclave having an inner cylinder made of Teflon (registered trademark), entirely uniformly heated by, for example, an oven or the like, and maintained at a hydrothermal synthesis temperature of from 160 to 200° C. for approximately from 24 to 60 hours, thereby enabling production of a zeolite.

The production step is preferably a step of producing a zeolite represented by the following Formula [2]:

$$xNa_2O \cdot Al_2O_3 \cdot ySiO_2 \cdot zH_2O \qquad [2]$$

in which x represents a positive number of from 0.5 to 5.0, y represents a positive number of from 80 to 150, and z represents a positive number of more than 20 to 50.

The zeolite represented by Formula [1] can be obtained by heating the zeolite represented by Formula [2] by a heating step described below.

[Heating Step]

The method for producing a deodorizer of the invention includes a heating step of heating the zeolite obtained at the production step at a temperature of 120° C. or more to obtain the zeolite represented by Formula [1].

The zeolite produced as described above is highly hydrophobic inorganic powder synthesized through a hydrothermal step, and has high heat resistance in itself. However, if heating, as in the invention, is not performed, any processed product does not exhibit excellent deodorizing performance. Due to this, it is necessary to heat the produced zeolite at a temperature of 120° C. or more before use thereof. Conditions for heating are 120° C. or more, preferably 120° C. or more for 1 hour or more, more preferably 130° C. or more for 3 hours or more, and still more preferably 150° C. or more for 3 hours or more. It is better that the higher the temperature is, the shorter the heating time is. However, there is no significant improvement in deodorizing effect even at a high temperature of 250° C. or more. Thus, the heating temperature may be 250° C. or less.

It is unknown why heat resistance is improved by heating after producing a zeolite. However, it seems that reduction in a trace amount of moisture or a low molecular weight compound on a zeolite surface enhances adsorption activity, thereby allowing excellent deodorizing performance to be exhibited.

2. Deodorizer Composition

The deodorizer of the invention is effective against VOC, and also can be used as a deodorizer composition by mixing with another deodorizer(s). Specific examples of other deodorizers that can be mixed with the deodorizer of the invention include basic gas deodorizers for deodorizing basic gases such as ammonia and trimethylamine. Examples of the basic gas deodorizers include tetravalent metal phosphate compounds insoluble or slightly soluble in water. Preferable specific examples of the tetravalent metal phosphate compounds include zirconium phosphate, titanium phosphate, and tin phosphate. These compounds are classified into crystalline compounds including various crystalline systems such as α-type crystal, β-type crystal, γ-type crystal, and nasicon-type crystal and amorphous compounds. Any of those having gas adsorbing properties can be mixed with the deodorizer of the invention.

The deodorizer of the invention can be mixed with a sulfur gas deodorizer for deodorizing sulfur gases such as hydrogen sulfide and methyl mercaptan to obtain a deodorizer composition. For example, the deodorizer of the invention can be mixed with silica gel, zinc oxide, copper silicate, or zinc silicate supporting at least one or more metal ions selected from copper, zinc, and manganese. As for silica gel, zinc oxide, copper silicate, and zinc silicate, the larger the specific surface area thereof, the higher the deodorizing performance thereof, which is thus preferable.

3. Deodorizing Processed Product

The deodorizer of the invention can be used as a final deodorizing product that is powdery or granular and that can be directly placed in a container such as a cartridge, and can be caused to exhibit the effect by allowing to stand in places such as the vicinities of indoor and outdoor odor-generating sources. Furthermore, the deodorizer of the invention can be used to produce a deodorizing processed product by blending in a resin, a fiber, a sheet, or the like, as described in detail below. In producing a deodorizing processed product, it is preferable to heat the zeolite at a temperature of 120° C. or more before processing and add the heated zeolite into a resin, a fiber, a paint, a sheet, or the like. The reason for this is that activating a zeolite surface before processing allows excellent deodorizing performance to be exhibited after processing. Additionally, when the deodorizer of the invention is stored in an open state for a long period, the deodorizing performance and heat resistance thereof will be reduced due to moisture absorption and the like, thereby causing a defect such as foaming in resin molding. Thus, the deodorizer is preferably stored in a sealed state.

(1) Resin Molded Product

As uses of the deodorizer of the invention, applications to resin-molded products are mentioned. Examples of a method for adding the deodorizer of the invention in a resin include a method of molding by directly charging a mixture of the resin and the deodorizer into a molding machine, a method of firstly pelletizing a mixture of the resin and the deodorizer by a molding machine to prepare a pelletized resin and then further molding the pelletized resin, and a method of molding after preparing a pelletized resin containing a high concentration of the deodorizer in advance and then mixing the pelletized resin with a main resin.

The kind of a resin to be used in resin-molded products is not particularly limited. Specifically, the kind of the resin may be any natural, synthetic, or semi-synthetic resin, and may be any thermoplastic or thermosetting resin. Specifically, the resin may be any molding resin, fiber resin, or rubber resin, and for example include molding or fiber resins such as ABS resin, AS resin, MBS resin, polyester, polyvinylidene chloride, polystyrene, polyacetal, polycarbonate, acrylic resin, methacrylic resin, fluororesin, polyurethane elastomer, polyester elastomer, melamine, urea resin, tetrafluoroethylene resin, unsaturated polyester resin, rayon, acetate, polyvinyl alcohol, cuprammonium rayon, triacetate, and vinylidene and rubber resins such as natural rubber, silicone rubber, styrene-butadiene rubber, ethylene propylene rubber, fluorine rubber, nitrile rubber, chlorosulfonated polyethylene rubber, butadiene rubber, synthetic natural rubber, butyl rubber, urethane rubber, and acrylic rubber. These resins may be either homopolymers or copolymers. In the case of copolymers, there is no particular limit to a polymerization ratio of respective copolymerization components.

In a resin composition as a mixture of any of the resins and the deodorizer as described above, the content of the deodorizer is not particularly limited, but preferably from 0.1 to 20 parts by mass, and more preferably from 0.5 to 10 parts by mass, with respect to 100 parts by mass of the resin. Typically, increasing the content allows deodorizing properties to be strongly exhibited and maintained for a long period. However, even when the content is increased to some extent or more, there is no significant difference in deodorizing effect.

In molding a mixture of the deodorizer and a resin, it is preferable to add a dispersant. The dispersant is a component that plays a significantly important role to allow deodorizing effect to be exhibited. When performing resin molding, the dispersant increases fluidity of the resin to prevent adhesion thereof to a molding machine, so that releasability from the mold is improved. As the dispersant, any conventionally used known compound can be used. Examples of the known compound include hydrocarbon-based dispersants such as liquid paraffin, natural paraffin, micro wax, polyethylene wax, chlorinated hydrocarbons, and fluorocarbon; fatty acid-based dispersants such as higher fatty acids and oxy-fatty acid; fatty acid amide-based dispersants such as fatty acid amide and alkyl bis-fatty acid amide; ester-based dispersants such as glyceride and ester wax; metal soaps; aliphatic alcohols; and partial esters of fatty acids and polyhydric alcohols, and any of the dispersants can be used. Among these dispersants, metal soaps are particularly preferred, and more preferred are metal soaps that are aliphatic metal salts having 10 or more carbon atoms. Specific examples of the more preferable metal soaps include cadmium stearate, cadmium laurate, cadmium ricinoleate, cadmium naphthenate, cadmium 2-ethylhexoic acid, barium stearate, barium laurate, barium ricinoleate, barium naphthenate, barium 2-ethylhexoic acid, calcium stearate, calcium laurate, calcium ricinoleate, zinc stearate, zinc laurate, zinc ricinoleate, zinc 2-ethylhexoic acid, lead stearate, dibasic lead stearate, lead naphthenate, tin stearate, and magnesium stearate. Calcium, zinc, magnesium, and the like are preferable as metal components of metal soaps since these substances are harmless.

These dispersants have been conventionally known as components for facilitating resin molding, as described above. In the invention, it has also been found that a resin composition obtained by blending any of the dispersants and the deodorizer together in a thermoplastic resin and a resin-molded product including the resin composition exhibit excellent deodorizing properties and maintain the properties over a long period. This fact can also be said to be a significantly effective technique.

The content of the dispersant is preferably from 0.01 to 10% by weight, and more preferably from 0.1 to 5% by weight, based on deodorizing resin composition (a total weight of the resin, the deodorizer, and the dispersant). When the content of the dispersant is within the range of from 0.01 to 10% by weight, the resin composition and the resin molded product can sufficiently exhibit deodorizing properties, and also physical properties of the resin molded product are not reduced. The dispersants may be used solely or in combination of a plurality of dispersants. Examples of combinations of the dispersants include combinations of ethylene glycol monostearate ester and various kinds of waxes and combinations of various kinds of wax-mixed products.

In order to improve the physical properties of the resin composition, other various additives such as an antibacterial agent, an antifungal agent, a photocatalyst, a pigment, a dye, an antioxidant, a light stabilizer, an antistatic agent, a foaming agent, an impact modifier, a glass fiber, a moisture-proof agent, and an extender can also be added if necessary.

Examples of molding methods that can be used to produce a deodorizing resin-molded product using the deodorizer of the invention include typical resin molding methods such as injection molding, extrusion molding, inflation molding, and vacuum molding. An obtained deodorizing resin-molded product can be used in various fields requiring deodorizing properties, and, for example, can be used in home electrical appliances such as air purifiers and refrigerators, common household goods such as trash boxes and drainer trays, various nursing care products such as portable toilets, daily commodities, and the like.

(2) Deodorant Fiber

One of deodorizing processed products of the invention is a deodorant fiber. In this case, a raw material fiber may be either a natural fiber or a synthetic fiber, and may be a short fiber, a long fiber, a composite fiber having a core-sheath structure, or the like. The method of providing deodorizing properties to a fiber by using the deodorizer of the invention is not particularly limited. For example, in a case in which the deodorizer of the invention is applied to the fiber in post-processing, a water-based or organic solvent-based suspension containing the deodorizer is allowed to adhere to a fiber surface by a method such as coating or dipping, and then a solvent is removed, thereby allowing the suspension to be coated on the fiber surface. In addition, in order to enhance the strength of adhesion to the fiber surface, a binder may be added and mixed. The pH of a water-based suspension containing the deodorizer is not particularly limited, but preferably around from 6 to 8 in order to allow the performance of the deodorizer to be sufficiently exhibited. As another method, the deodorizer of the invention is kneaded into a molten liquid fiber resin or a dissolved fiber resin solution by heating and melting or the like, and the resulting resin product is fiberized to obtain a fiber provided with deodorizing properties. As methods for fiberization, there are heating-melting spinning, dry spinning, and wet spinning, and a method therefor may be selected as appropriate depending on the kind of a resin to be used.

The content of the deodorizer in the deodorant fiber is preferably from 0.1 to 20 parts by mass, and more preferably from 0.5 to 10 parts by mass with respect to 100 parts by mass of a fiber resin. When the content thereof is within the range of from 0.1 to 20 parts by mass, the fiber can be provided with deodorizing properties without reducing strength thereof.

A deodorant fiber using the deodorizer of the invention can be used in various fields requiring deodorizing properties, and can be used in many fiber products, such as underwear, pantyhose, socks, futons, futon covers, cushions, blankets, carpets, curtains, sofas, car seats, air filters, and nursing care clothes.

(3) Deodorant Coating

As a deodorizing processed product of the invention, a deodorizing paint is also mentioned. In producing a deodorant coating, an oil or a resin as a main component of a coating vehicle used is not particularly limited, and may be a natural vegetable oil, a natural resin, a semi-synthetic resin, or a synthetic resin, and may be either a thermoplastic resin or a thermosetting resin. Examples of oils and resins that can be used include drying oils or semi-drying oils, such as linseed oil, Chinese wood oil, and soybean oil, rosin, nitrocellulose, ethylcellulose, cellulose acetate butyrate, benzyl cellulose, novolac-type or resol-type phenolic resins, alkyd resins, amino alkyd resins, acrylic resins, vinyl chloride, silicone resins, fluororesins, epoxy resins, urethane resins, saturated polyester resins, melamine resins, and polyvinylidene chloride resins.

The deodorizer of the invention can be used in both liquid paint and powder paint. A deodorant coating composition using the deodorizer of the invention may be of a type that will be cured by any mechanism. Specific examples thereof include oxidative polymerization type, moisture polymerization type, heat curing type, catalytically curing type, UV curing type, and polyol curing type. A pigment, a dispersant, and other additives used in the coating composition are not particularly limited, except for additives that can chemically react with a deodorizing substance (for example, particulate zinc oxide) used in combination. A paint composition using the deodorizer of the invention or the deodorizer composition thereof can be easily prepared. Specifically, it is enough to thoroughly disperse and mix the deodorizer or the deodorizer composition and coating components in a typical mixing device such as a ball mill, a roll mill, a disper, or a mixer.

The content of the deodorizer in the deodorant coating is not particularly limited. Typically, increasing the amount thereof allows deodorizing properties to be strongly exhibited and maintained for a long period. However, even when a certain amount or more of the deodorizer is included, there is no significant difference in deodorizing effect. In addition, from the viewpoint of gloss and strength of a coated film, the content of the deodorizer is preferably from 0.1 to 20 parts by mass, and more preferably from 0.5 to 10 parts by mass based on 100 parts by mass of the paint composition. A deodorant coating including the deodorizer of the invention is usable in various fields requiring deodorizing properties, and, for example, can be used for inner walls and outer walls of buildings, vehicles, trains, and the like, waste incineration facilities, kitchen garbage containers, and the like.

(4) Deodorant Sheet

A deodorizing sheet is one of the deodorizing processed products. The material, structure, and the like of a sheet material used as a raw material are not limited. Preferable materials are resins, paper, and the like, or composite products thereof, and porous materials. Preferable specific examples of the sheet material include Japanese paper, synthetic paper, nonwoven fabrics, and resin films, and particularly preferable sheet materials are paper made of natural pulp and/or synthetic pulp. The use of natural pulp is advantageous in that a powder of deodorizer particles is sandwiched between finely branched pieces of fiber, and serves as a practical support without particularly using any binder, whereas synthetic pulp is advantageous in having excellent chemical resistance. In the case of use of synthetic pulp, it may be difficult to support the deodorizer particles by sandwiching the powder between the pieces of fiber. Due to this, adhesion between the powder and the fiber may be increased by melting a part of the fiber in a drying step after paper-making, or an other thermosetting resin fiber may be mixed in a part of the fiber. With the use of natural pulp and synthetic pulp mixed in an appropriate ratio as mentioned above, paper provided with various characteristics adjusted can be obtained. Typically, increasing the percentage of synthetic pulp can provide paper excellent in strength, water resistance, chemical resistance, oil resistance, and the like.

On the other hand, increasing the percentage of natural pulp can provide paper excellent in water absorption, gas permeability, hydrophilicity, moldability, texture, and the like.

The method of supporting the deodorizer of the invention on the above sheet material is not particularly limited. The deodorizer of the invention may be supported either at the time of production of a sheet or after production thereof. In the case of supporting the deodorizer on paper, examples of a supporting method therefor include introduction of the deodorizer in any step of a paper-making process and application, immersion, or spraying of a liquid containing a binder and the deodorizer dispersed therein onto paper produced in advance.

As for the amount of the deodorizer of the invention supported on a sheet material, typically, increasing supporting the amount allows deodorizing properties to be strongly exhibited and maintained for a long period. However, even when a certain amount or more of the deodorizer is supported, there is no significant difference in deodorizing effect. Thus, in the case of supporting the deodorizer on the surface of a sheet and the entire inside thereof in a paper-making process, the supporting amount of the deodorizer is preferably from 0.1 to 10 parts by mass based on 100 parts by mass of the sheet. In the case of supporting the deodorizer on only the surface of a sheet by coating or the like in post-processing, the amount thereof is preferably from 0.05 to 10 $g/m^2$. A deodorant sheet produced by using the deodorizer of the invention can be used in various fields requiring deodorizing properties. Examples of uses of such a deodorant sheet include medical package paper, food package paper, electric equipment packing paper, nursing care paper products, freshness-keeping paper, paper clothes, air purifying filters, wall paper, tissue paper, and toilet tissue.

EXAMPLES

Hereinafter, the present invention will be described by Examples, but is not limited thereto. In the following description, "parts" and "%" are based on mass unless otherwise noted.

1. Evaluation Method (1) Powder X-Ray Diffraction

A crystal system of a zeolite produced can be confirmed by powder X-ray diffraction analysis. Powder X-ray diffraction analysis can be performed according to provisions of JIS K 0131 (established in 1996). The provisions of JIS do not describe a voltage applied to an X-ray tube. In the present analysis, X-ray diffraction measurement was performed using a CuKα ray generated at a Cu target X-ray tube voltage of 40 kv and a current value of 150 mA. If a sample includes a crystalline substance, a diffraction peak having an acute shape appears on an X-ray diffraction diagram. Thus, from the obtained powder X-ray diffraction diagram, a diffraction angle 2θ of the diffraction peak can be determined, and, based on a relationship of $\lambda=2d \sin \theta$, a spacing d of crystal is calculated to allow identification of the crystal system. The "λ" of the CuKα is 1.5418 Å.

(2) Particle Diameter

A median diameter and a maximum particle diameter of zeolite were calculated by measuring by a laser diffraction particle size analyzer, and analyzing based on volume.

(3) BET Specific Surface Area

Measurement was performed using AUTOSORB-1 manufactured by Quantanchrome Instruments Co., Ltd. according to JIS Z 8830 (amended in 2013) "Determination of the specific surface area of powders (solids) by gas adsorption".

(4) Deodorizing Capacity

An amount of 0.2 g of a deodorizer powder was placed in a vinylidene chloride-laminated bag with a volume of approximately 4 L, and 3 liters of air containing n-butane as a test gas at a concentration of 10 ppm was injected into the bag, which then allowed to stand for 2 hours at room temperature (from 15 to 25° C.).

Subsequently, gas concentrations of n-butane remaining in the vinylidene chloride-laminated bag containing the deodorizer and a separately prepared empty vinylidene chloride-laminated bag were measured by a gas detector tube (manufactured by Gastec Corporation; hereinafter the same company's product was used), and a deodorizing capacity was calculated by the following Formula [3] (unit mL/g; "mL" indicates a volume of gas in the standard state):

$$(C-C_0) \times V/W \qquad [3]$$

C: Gas concentration in the vinylidene chloride-laminated bag containing the deodorizer $C_0$: Gas concentration in the empty vinylidene chloride-laminated bag V: Gas volume (mL)

W: Deodorizer weight (g)

In a case in which the test gas was xylene, 0.02 g of the deodorizer power was used to evaluate in the same manner.

(5) Deodorizing Rate

Three resin-molded plates (10 cm long×10 cm width×2 mm thick) were placed in a vinylidene chloride-laminated bag with a volume of approximately 4 L, and 3 liters of air containing acetaldehyde as a test gas at a concentration of 14 ppm was injected into the bag, which then allowed to stand for 2 hours at room temperature (from 15 to 25° C.).

Subsequently, gas concentrations of n-butane remaining in the vinylidene chloride-laminated bag containing the resin plates that contain the deodorizer and a vinylidene chloride-laminated bag of resin plates not containing the deodorizer were measured by the gas detector tube, and a deodorizing rate (%) was calculated by the following Formula (4):

$$(C_B - C_A)/C_B \times 100 \qquad [4]$$

$C_A$: Acetaldehyde gas concentration in use of resin plates containing deodorizer $C_B$: Acetaldehyde gas concentration in use of resin plates without deodorizer (6) Deodorizing Intensity One resin-molded plate (10 cm long×10 cm width×2 mm thick) was placed in a polyester bag with a volume of approximately 1 L and sealed. After allowing the bag to stand at 50° C. for 3 hours, an odor in the bag was evaluated in a sensory manner. An odor obtained in the case of use of a resin plate without the deodorizer was defined as an odor intensity of 4 in a six-grade odor intensity measurement method (Table 1) to determine the level of the odor. Evaluation was performed by four people, and an average value was defined as a deodorizing intensity.

TABLE 1

| Deodorizing intensity | Level of odor |
|---|---|
| 0 | Odorless |
| 1 | Perceivable odor (Sensing threshold concentration) |
| 2 | Weak but barely discernible odor (Recognition threshold concentration) |
| 3 | Easily discernible odor |
| 4 | Rather strong odor |
| 5 | Very strong odor |

2. Production of Deodorizer

Comparative Examples 1, 2, 4, and 5

A mixed aqueous solution of sodium hydroxide and sodium aluminate and a colloidal silica sol liquid were added dropwise to tetrapropylammonium bromide (TPABr) to prepare an aqueous mixture. The amount of each raw material used was adjusted so as to give a molar composition ratio shown in Table 2. The obtained aqueous mixture was transferred to an autoclave, and heated at 170° C. for 60 hours to synthesize zeolites of Comparative Examples 1, 2, 4, and 5.

Comparative Example 3

A mixed aqueous solution of sodium hydroxide, ammonium chloride, and sodium aluminate and a colloidal silica sol liquid were added dropwise to tetrapropylammonium bromide (TPABr) to prepare an aqueous mixture. The amount of each raw material used was adjusted so as to give a molar composition ratio shown in Table 2. The obtained aqueous mixture was transferred to an autoclave, and heated at 170° C. for 60 hours to synthesize a zeolite of Comparative Example 3. In Table 2, the symbol "-" indicates that no corresponding compound is included.

TABLE 2

| Composition ratio | $SiO_2/Al_2O_3$ | $TPABr/SiO_2$ | $Na_2O/SiO_2$ | $H_2O/SiO_2$ | $(NH_4)_2O/SiO_2$ |
|---|---|---|---|---|---|
| 1 | 130 | 0.1 | 0.2 | 150 | — |
| 2 | 160 | 0.1 | 0.2 | 150 | — |
| 3 | 130 | 0.1 | 0.1 | 150 | 0.2 |
| 4 | 60 | 0.1 | 0.2 | 150 | — |
| 5 | 250 | 0.1 | 0.2 | 150 | — |

The obtained zeolites were all confirmed to be crystalline particles from results of the powder X-ray diffraction analysis. Zeolites obtained from synthetic mother liquids of respective composition ratios 1 to 5 were defined as those of Comparative Examples 1 to 5, and the compositions thereof were obtained through a metal content analysis to obtain the following results:

Comparative Example 1: $2.1Na_2O \cdot Al_2O_3 \cdot 98SiO_2 \cdot 28H_2O$
Comparative Example 2: $1.5Na_2O \cdot Al_2O_3 \cdot 113SiO_2 \cdot 44H_2O$
Comparative Example 3: $1.2NH_4 \cdot 0.2Na_2O \cdot Al_2O_3 \cdot 97SiO_2 \cdot 25H_2O$
Comparative Example 4: $2.6Na_2O \cdot Al_2O_3 \cdot 42SiO_2 \cdot 20H_2O$
Comparative Example 5: $0.9Na_2O \cdot Al_2O_3 \cdot 222SiO_2 \cdot 15H_2O$ In addition, results of measurement of particle size distributions of the zeolites are shown in Table 3.

TABLE 3

| | Median diameter (μm) | Maximum particle diameter (μm) |
|---|---|---|
| Comparative Example 1 | 1.7 | 7.8 |
| Comparative Example 2 | 1.4 | 6.2 |
| Comparative Example 3 | 2.7 | 16.6 |
| Comparative Example 4 | 2.7 | 13.8 |
| Comparative Example 5 | 5.1 | 26.1 |

Examples 1 to 4

The respective zeolites of Comparative Examples 1 and 2 were heated at 120° C. for 6 hours to obtain deodorizers of Examples 1 and 2. In addition, the respective zeolites of Comparative Examples 1 and 2 were heated at 180° C. for 3 hours to obtain deodorizers of Examples 3 and 4. No changes in particle sizes due to heating were observed.

Example 1: $2.0Na_2O.Al_2O_3.99SiO_2.10H_2O$
Example 2: $1.5Na_2O.Al_2O_3.114SiO_2.18H_2O$
Example 3: $2.2Na_2O.Al_2O_3.98SiO_2.9H_2O$
Example 4: $1.6Na_2O.Al_2O_3.114SiO_2.7H_2O$ Comparative Examples 6 to 8

The respective zeolites of Comparative Examples 3 to 5 were heated at 180° C. for 3 hours to obtain deodorizers of Comparative Examples 6 to 8. No changes in particle sizes due to heating were observed.

Comparative Example 6: $1.1NH_4.0.2Na_2O.Al_2O_3.97SiO_2.3H_2O$
Comparative Example 7: $2.6Na_2O.Al_2O_3.43SiO_2.14H_2O$
Comparative Example 8: $0.9Na_2O.Al_2O_3.222SiO_2.5H_2O$ Table 4 shows deodorizing capacities of the obtained deodorizers.

TABLE 4

|  | n-butane (mL/g) | Xylene (mL/g) |
| --- | --- | --- |
| Example 1 | 10 | 3.0 |
| Example 2 | 11 | 4.0 |
| Example 3 | 11 | 4.0 |
| Example 4 | 12 | 4.5 |
| Comparative Example 1 | 5 | 1.5 |
| Comparative Example 2 | 3 | 1.0 |
| Comparative Example 3 | 4 | 1.5 |
| Comparative Example 4 | 3 | 1.0 |
| Comparative Example 5 | 6 | 1.0 |
| Comparative Example 6 | 5 | 1.5 |
| Comparative Example 7 | 3 | 1.0 |
| Comparative Example 8 | 6 | 1.0 |

Examples 5 to 8 and Comparative Examples 9 to 13

Two parts of the deodorizer of Example 1 were added to 100 parts of polypropylene (PP) resin and the mixture was injection molded at 200° C. to mold a plate having a thickness of 2 mm for evaluation (Example 5). The deodorizers of Examples 2 to 4 and Comparative Examples 1 to 4 were also evaluated in the same manner (Examples 6 to 8 and Comparative Examples 9 to 12). In addition, a resin-molded plate containing no deodorizer was defined as Comparative Example 13. In Example 6, 0.2 parts of magnesium stearate were added as a dispersant. Table 5 shows the results.

TABLE 5

| | Kind of resin | Kind of deodorizer | Addition of dispersant | Deodorizing rate (%) |
| --- | --- | --- | --- | --- |
| Example 5 | PP resin | Example 1 | No | 70 |
| Example 6 | | Example 2 | Yes | 75 |
| Example 7 | | Example 3 | No | 85 |
| Example 8 | | Example 4 | No | 95 |
| Comparative Example 9 | | Comparative Example 1 | No | 35 |
| Comparative Example 10 | | Comparative Example 2 | No | 20 |
| Comparative Example 11 | | Comparative Example 3 | No | 35 |

TABLE 5-continued

| | Kind of resin | Kind of deodorizer | Addition of dispersant | Deodorizing rate (%) |
| --- | --- | --- | --- | --- |
| Comparative Example 12 | | Comparative Example 4 | No | 30 |
| Comparative Example 13 | | None | No | 0 |

Examples 9 to 12 and Comparative Examples 14 to 18

Two parts of the deodorizer of Example 1 were added to 100 parts of polyolefin-based elastomer, and the mixture was injection molded at 200° C. to mold a plate having a thickness of 2 mm for evaluation (Example 9). The deodorizers of Examples 2 to 4 and Comparative Examples 1 to 4 were also evaluated in the same manner (Examples 10 to 12 and Comparative Examples 14 to 17). In addition, a resin-molded plate containing no deodorizer was defined as Comparative Example 18. In Example 10, 0.2 parts of magnesium stearate were added as a dispersant. Table 6 shows the results.

TABLE 6

| | Kind of resin | Kind of deodorizer | Addition of dispersant | Odor intensity |
| --- | --- | --- | --- | --- |
| Example 9 | Polyolefin-based elastomer | Example 1 | No | 2 |
| Example 10 | | Example 2 | Yes | 1.5 |
| Example 11 | | Example 3 | No | 1 |
| Example 12 | | Example 4 | No | 1 |
| Comparative Example 14 | | Comparative Example 1 | No | 3.5 |
| Comparative Example 15 | | Comparative Example 2 | No | 3 |
| Comparative Example 16 | | Comparative Example 3 | No | 4 |
| Comparative Example 17 | | Comparative Example 4 | No | 3 |
| Comparative Example 18 | | None | No | 4 |

The deodorizers of Examples have high VOC-adsorbing performance, and also exhibit deodorizing effect even in processed products obtained by adding to resin and heat-molding at a processing temperature of 200° C. On the other hand, the deodorizers of Comparative Examples have low adsorbing performance, and when added to resin and heat-molded, sufficient deodorizing effect cannot be obtained.

INDUSTRIAL APPLICABILITY

The deodorizer of the invention has high adsorption performance and has heat resistance. Additionally, a deodorizing processed product obtained by processing using the deodorizer has excellent deodorizing effect. Accordingly, deodorizing processed products can be obtained through various materials and processing conditions, and can be applied to VOC reduction in environments and the like.

The invention claimed is:

1. A deodorizer comprising a zeolite represented by the following Formula [1],
    wherein the zeolite is obtained by producing a zeolite and then heating the produced zeolite at a temperature of 120° C. or more:

$$xNa_2O.Al_2O_3.ySiO_2.zH_2O \qquad [1]$$

wherein x represents a positive number of from 0.5 to 5.0,
y represents a positive number of from 95 to 120, and
z represents a positive number of from 1 to 20.

2. A deodorizer composition comprising the deodorizer according to claim 1 and at least one of a basic gas deodorizer or a sulfur gas deodorizer.

3. A deodorizing processed product comprising the deodorizer according to claim 1.

4. A method for producing a deodorizer comprising, in the following order:
a production step of producing a zeolite; and
a heating step of heating the zeolite obtained at the production step at a temperature of 120° C. or more to obtain a zeolite represented by Formula [1]:

$$x\text{Na}_2\text{O}\cdot\text{Al}_2\text{O}_3\cdot y\text{SiO}_2\cdot z\text{H}_2\text{O} \qquad [1]$$

wherein x represents a positive number of from 0.5 to 5.0,
y represents a positive number of from 95 to 120, and
z represents a positive number of from 1 to 20.

5. A method for producing a deodorizing processed product comprising: producing a zeolite represented by Formula [1], then heating the zeolite at a temperature of 120° C. or more before processing, and blending the obtained zeolite in a resin, a fiber, a coating, or a sheet, $$x\text{Na}_2\text{O}\cdot\text{Al}_2\text{O}_3\cdot y\text{SiO}_2 z\text{H}_2\text{O} \qquad [1]$$

wherein x represents a positive number of from 0.5 to 5.0,
y represents a positive number of from 95 to 120, and
z represents a positive number of from 1 to 20.

\* \* \* \* \*